(12) United States Patent
Dong

(10) Patent No.: US 10,881,346 B2
(45) Date of Patent: Jan. 5, 2021

(54) SLEEP AIDING DEVICE AND METHOD THEREOF, SERVER AND SYSTEM

(71) Applicant: BOE TECHNOLOGY GROUP CO., LTD., Beijing (CN)

(72) Inventor: Wenchu Dong, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 156 days.

(21) Appl. No.: 16/061,383

(22) PCT Filed: Dec. 8, 2017

(86) PCT No.: PCT/CN2017/115258
§ 371 (c)(1),
(2) Date: Jun. 12, 2018

(87) PCT Pub. No.: WO2018/205586
PCT Pub. Date: Nov. 15, 2018

(65) Prior Publication Data
US 2019/0298255 A1 Oct. 3, 2019

(30) Foreign Application Priority Data

May 10, 2017 (CN) .......................... 2017 1 0325922

(51) Int. Cl.
*A61B 5/00* (2006.01)
*A61B 5/04* (2006.01)
(Continued)

(52) U.S. Cl.
CPC .............. *A61B 5/4809* (2013.01); *A61B 5/00* (2013.01); *A61B 5/0022* (2013.01);
(Continued)

(58) Field of Classification Search
None
See application file for complete search history.

(56) References Cited

U.S. PATENT DOCUMENTS

2010/0145167 A1* 6/2010 Im ........................ A47G 9/1045
600/301
2014/0221779 A1 8/2014 Schoonover
(Continued)

FOREIGN PATENT DOCUMENTS

CN 101584903 A 11/2009
CN 102247122 A 11/2011
(Continued)

OTHER PUBLICATIONS

International Search Report dated Feb. 24, 2018.
First Chinese Office Action dated Nov. 27, 2019.

*Primary Examiner* — Brian T Gedeon
(74) *Attorney, Agent, or Firm* — Dilworth & Barrese, LLP.; Michael J. Musella, Esq.

(57) ABSTRACT

A sleep aiding device and a method thereof, a server and a method thereof and a sleep aiding system. The sleep aiding device includes: a physical-sign detecting part, configured to detect physical sign data associated with a user; a brainwave detecting part, configured to detect brainwave signal data associated with the user; and a display and play part, configured to: receive a display and play instruction, and adjust at least one of a display mode and a play mode of the sleep aiding device according to the display and play instruction. The display and play instruction is generated according to at least one of the physical sign data and the brainwave signal data.

17 Claims, 6 Drawing Sheets

(51) Int. Cl.
    *G06F 3/01*         (2006.01)
    *A61B 5/0476*     (2006.01)
    *A61B 5/0205*     (2006.01)
    *A61M 21/02*     (2006.01)
    *H04M 1/725*     (2006.01)

(52) U.S. Cl.
    CPC ........ *A61B 5/0205* (2013.01); *A61B 5/04001* (2013.01); *A61B 5/0476* (2013.01); *A61B 5/6892* (2013.01); *A61B 5/742* (2013.01); *A61M 21/02* (2013.01); *G06F 3/015* (2013.01); *H04M 1/725* (2013.01); *G06F 2203/011* (2013.01)

(56) References Cited

U.S. PATENT DOCUMENTS

| | | | |
|---|---|---|---|
| 2014/0316191 A1 | 10/2014 | De Zambotti et al. | |
| 2015/0187199 A1* | 7/2015 | Chang | A61M 21/02 340/575 |
| 2016/0081616 A1* | 3/2016 | Li | A61B 5/4812 600/301 |

FOREIGN PATENT DOCUMENTS

| | | | |
|---|---|---|---|
| CN | 103372258 A | 10/2013 | |
| CN | 104257381 A | 1/2015 | |
| CN | 204233577 U | 4/2015 | |
| CN | 104759017 A | 7/2015 | |
| CN | 204655741 U | 9/2015 | |
| CN | 105590640 A | 5/2016 | |
| CN | 103137157 A | 6/2016 | |
| CN | 106039524 A | 10/2016 | |

\* cited by examiner

US 10,881,346 B2
// 1

SLEEP AIDING DEVICE AND METHOD THEREOF, SERVER AND SYSTEM

TECHNICAL FIELD

Embodiments of the present disclosure relate to a sleep aiding device and a method thereof, a server and a method thereof, and a sleep aiding system.

BACKGROUND

Most people in modern society have difficulty in falling asleep and have a low sleep quality, due to work stress and other reasons; particularly, more and more young people rely on display screens and stay up late. In order to help people to fall asleep quickly or improve the sleep quality, more and more sleep aiding products are available.

SUMMARY

Embodiments of the disclosure provide a sleep aiding device, comprising: a physical-sign detecting part, configured to detect physical sign data associated with a user; a brainwave detecting part, configured to detect brainwave signal data associated with the user; and a display and play part, configured to: receive a display and play instruction, wherein the display and play instruction is generated according to at least one of the physical sign data and the brainwave signal data; and adjust at least one of a display mode and a play mode of the sleep aiding device according to the display and play instruction.

For example, the sleep aiding device further comprises a rest appliance.

For example, the physical-sign detecting part includes a physical-sign detecting sub-part; and the physical-sign detecting sub-part includes a sensor configured for detecting the physical sign data associated with the user.

For example, the physical-sign detecting part further includes a fixing sub-part; and the fixing sub-part is configured to fix the physical-sign detecting sub-part to the physical-sign detecting part, and fix the physical-sign detecting part to the rest appliance.

For example, the brainwave detecting part includes a pillow apparatus and a brainwave detecting sub-part connected with the pillow apparatus; the brainwave detecting sub-part includes a frame and a brainwave detecting electrode fixed to the frame; and the brainwave detecting electrode is configured to detect the brainwave signal data associated with the user.

For example, the brainwave detecting sub-part sends the brainwave signal data associated with the user to the server; or the brainwave detecting sub-part sends the brainwave signal data associated with the user to the display and play part, and the display and play part sends the brainwave signal data associated with the user to the server.

For example, the display and play part includes a signal transceiver, a display device and a player; the signal transceiver is configured to send the physical sign data after amplification processing to the server, and receive the display and play instruction from the server; the display device is configured to activate and adjust the display mode according to the display and play instruction, so that the display mode matches the physical sign data and the brainwave signal data associated with the user; and the player is configured to activate and adjust the play mode according to the display and play instruction, so that the play mode matches the physical sign data and the brainwave signal data associated with the user.

For example, the display device includes a projecting device or a display.

For example, the display and play part further includes a signal amplifier, and the signal amplifier is configured to perform amplification processing on the physical sign data; the display device is further configured to: automatically rotate and detect a surrounding environment when activating the display mode; and adjust brightness of a display image according to at least one of brightness of the surrounding environment and the display and play instruction; and the player is further configured to adjust play content and play volume according to the display and play instruction when activating the play mode.

For example, content of the display image and the play content each include at least one of pre-stored content, content obtained through a network, and content played by a television.

For example, the physical sign data associated with the user includes at least one of pulse signal data, body temperature data, or blood pressure data associated with the user.

For example, the display and play instruction instructs at least one of turning on or off of a display function, the content and a source of a display image, brightness of the display image, turning on or off of a play function, play content and its source, or a play volume.

Embodiments of the disclosure further provide a sleep aiding method, used in the sleep aiding device described above, comprising: detecting physical sign data associated with a user; detecting brainwave signal data associated with the user; receiving a display and play instruction, wherein the display and play instruction is generated according to at least one of the physical sign data and the brainwave signal data; and adjusting at least one of a display mode and a play mode of the sleep aiding device according to the display and play instruction.

For example, before receiving the display and play instruction, the method further comprises: performing amplification processing on the detected physical sign data; sending the physical sign data after amplification processing to a server; and sending the brainwave signal data associated with the user to the server.

Embodiments of the disclosure further provide a server, comprising: a receiving device, configured to receive physical sign data and brainwave signal data associated with a user; a generating device, configured to determine a sleep-awake degree associated with the user according to the physical sign data and the brainwave signal data, and generate a display and play instruction according to the sleep-awake degree associated with the user; and a sending device, configured to send the display and play instruction.

Embodiments of the disclosure further provide a server-side sleep aiding service method, used in the server described above, comprising: receiving physical sign data associated with a user; receiving brainwave signal data associated with the user; determining a sleep-awake degree associated with the user according to at least one of the physical sign data and the brainwave signal data; generating a display and play instruction according to the sleep-awake degree associated with the user; and sending the display and play instruction.

Embodiments of the disclosure further provide a sleep aiding service system, comprising: the sleep aiding device described above; and a server, including: a receiving device, configured to receive physical sign data and brainwave signal data associated with a user; a generating device, configured to determine a sleep-awake degree associated with the user according to at least one of the physical sign data and the brainwave signal data, and generate a display and play instruction according to the sleep-awake degree associated with the user; and a sending device, configured to send the display and play instruction.

BRIEF DESCRIPTION OF THE DRAWINGS

In order to illustrate the technical solutions in the embodiments of the present disclosure or the existing arts more clearly, the drawings needed to be used in the description of the embodiments or the existing arts will be briefly described in the following; it is obvious that the drawings described below are only related to some embodiments of the present disclosure, for one ordinary skilled person in the art, other drawings can be obtained according to these drawings without making other inventive work.

REFERENCE SIGNS

Figure 1:
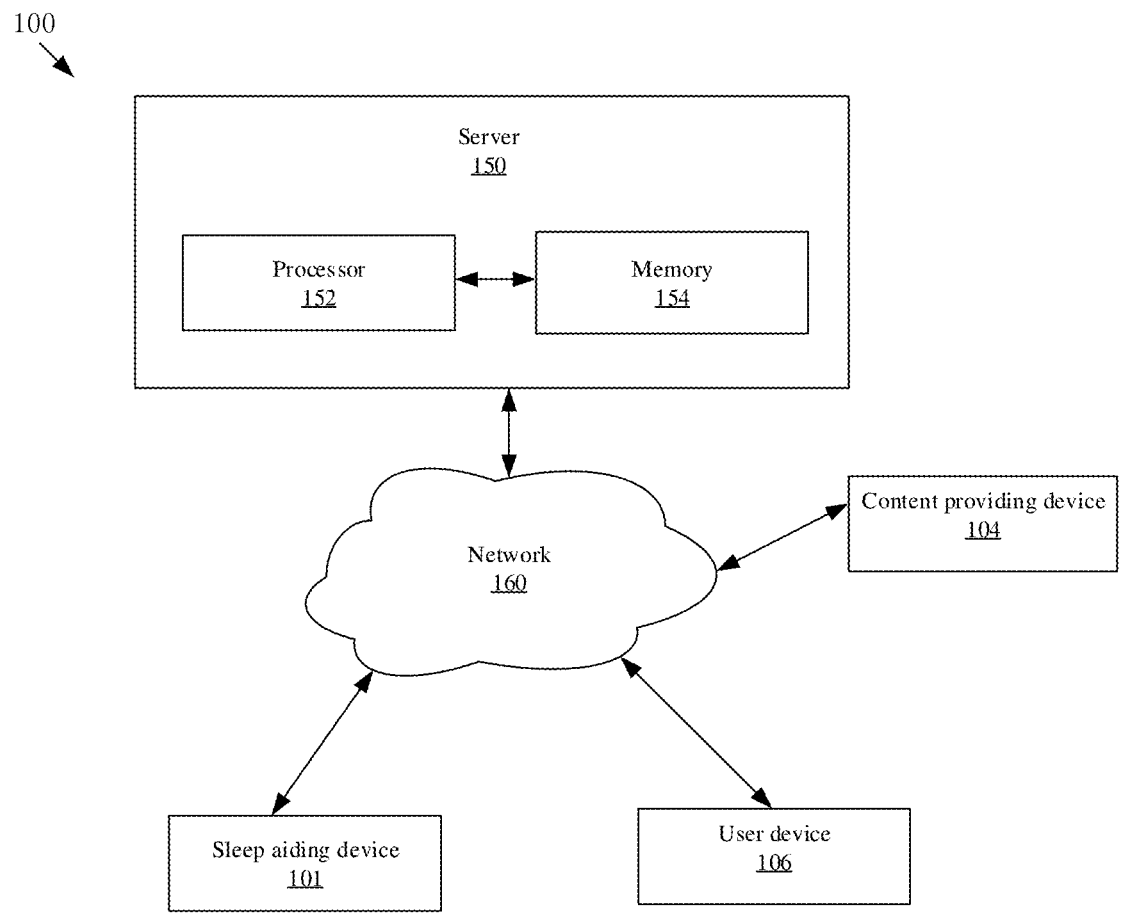
FIG. 1 is a schematic block diagram illustrating hardware of a sleep aiding service system provided by an embodiment of the present disclosure.

Sleep aiding device 101, content providing device 104, user device 106, server 150, processor 152, memory 154, network 160, physical-sign detecting part 202, brainwave detecting part 204, display and play part 206, rest appliance 208, controller 210, generating device 212, physical-sign detecting sub-part 2022, sensor 2024, fixing sub-part 2026, pillow apparatus 2042, brainwave detecting sub-part 2044, frame 2046, brainwave detecting electrode 2048, signal amplifier 2062, signal transceiver 2064, display device 2066, player 2068, receiving device 402, generating device 406, sending device 408, sleep aiding system 600 and projection plane 702.

DETAILED DESCRIPTION

Hereafter, the technical solutions of the embodiments of the present disclosure will be described in a clearly and fully understandable way in connection with the drawings related to the embodiments of the disclosure. It is obvious that the described embodiments are just a part but not all of the embodiments of the present disclosure. Based on embodiments of the present disclosure, all other embodiments obtained by those skilled in the art without making other inventive work should be within the scope of the present disclosure.

A sleep aiding device and a method thereof, a server and a method thereof, and a sleep aiding system provided by embodiments of the present disclosure are capable of automatically adjusting a display mode and a play mode according to changes of a sleep-awake degree of a user (e.g., a fully awake state, a semi-awake state, a shallow sleep state, and a deep sleep state, etc.), so that the display mode and the play mode match a current sleep-awake degree of the user, so as to help the user to fall asleep quickly and improve sleep quality. For example, display content and display brightness may be adjusted, and play content and play volume may be adjusted, so that the display content and the display brightness as well as the play content and the play volume match the current sleep-awake degree of the user. For another example, as the user gradually enters the deep sleep state from the fully awake state, brightness of a display image may be gradually reduced until the display device is turned off; the play volume is gradually reduced, and the play content is gradually replaced with a music having a more soothing rhythm, until the player is turned off.

Hereinafter, the sleep aiding device and the method thereof, the server and the method thereof, and the sleep aiding system provided by the embodiments of the present disclosure will be described in detail with reference to the accompanying drawings.

FIG. 1 is a schematic block diagram of hardware of a sleep aiding service system 100 provided by an embodiment of the present disclosure. For example, the sleep aiding service system 100 may be an intelligent sleep aiding service system. As shown in FIG. 1, the system 100 may comprise a sleep aiding device 101, a content providing device 104, a user device 106 and a server 150. For example, the sleep aiding device 101 may be an intelligent sleep aiding device. Respective devices and/or servers in the system 100 may be connected through a network 160. Respective devices and/or servers of the system 100 may communicate with one another directly or indirectly; for example, respective devices and/or servers of the system 100 may send and receive data and/or signals to one another via the network 160.

The network 160 may include a wireless network, a wired network, and/or any combination of the wireless network and the wired network. For example, the network 160 may include a local area network, the Internet, a telecommunication network, Internet of Things based on the Internet and/or the telecommunication network, and/or any combination of the above-described networks. Types and functions of the network 160 will not be limited here in the present disclosure.

The server 150 may be a computing device that includes a processor and a memory. For example, the server 150 may be a server in a local area network or a cloud server. FIG. 1 shows that server 150 includes a processor 152 and a memory 154.

The processor 152 may process data signals, and may include various computing structures, for example, a complex instruction set computer (CISC) structure, a reduced instruction set computer (RISC) structure, or a structure implementing a combination of multiple instruction sets. In some embodiments, the processor 152 may also be a microprocessor, for example, an X86 processor or an ARM processor, or may be a digital signal processor (DSP), and the like. The processor 152 may control other parts in the server 150 to execute a desired function.

The memory 154 may preserve instructions and/or data executed by the processor 152. For example, the memory 154 may include one or more computer program products, and the computer program products may include various forms of computer-readable storage media, for example, a volatile memory and/or a non-volatile memory. The volatile memory may include, for example, a random access memory (RAM) and/or a cache, and the like. The non-volatile memory may include, for example, a read-only memory (ROM), a hard disk, a flash memory, and the like. One or more computer program instructions may be stored on the computer-readable storage medium, and the processor 152 may execute the program instructions, to implement a sleep aiding function and/or other desired functions as described below. Various application programs and various data, for example, various data used and/or generated by the application programs, and the like, may also be stored in the computer-readable storage medium.

The sleep aiding device 101 may be a device for helping a user to enter a sleep state and/or to improve sleep quality. The sleep aiding device 101 will be described in detail below with reference to FIG. 2A to FIG. 2C and FIG. 7 to FIG. 9.

The content providing device 104 may be a computing device including a processor and a memory. For example, the content providing device 104 may be a television, a desktop computer, a notebook computer, a smart phone, a game controller, a music player, a tablet computer, and other devices including a processor and a memory. For another example, the content providing device 104 may be a server. The content providing device 104 is configured to provide the sleep aiding device 101 with display content and/or play content. For example, the content providing device 104 is configured to provide the sleep aiding device 101 with video content (e.g., a movie, a short film, a TV program, and the like) and/or audio content (e.g., a podcast, music, a radio program, and the like). In some examples, the content providing device 104 may be integrated in the sleep aiding device 101. In other examples, the content providing device 104 and the sleep aiding device 101 are separate devices.

The user device 106 may be a computing device that includes a processor and a memory. For example, the user device 106 may be a television, an intelligent household appliance, a desktop computer, a notebook computer, a smart phone, a tablet computer, a game controller, a music player (e.g., an mp3 player, etc.), and other terminals including a processor and a memory (e.g., a mobile terminal and a smart terminal). In some embodiments, the user device 106 may include a processor, a memory, and other parts such as an input device and an output device. In some examples, the user may use the user device 106 for controlling or operating the sleep aiding device 101. For example, the user may use an application (app) in the user device 106 for activating or deactivating a display function and a play function in the sleep aiding device 101, selecting a display device (e.g., selecting a projecting device and a projection plane thereof), and selecting display content and play content, and the like.

It is worth noting that, the user device 106 and the content providing device 104 may be a same device or different devices, which will not be limited here in the present disclosure.

In some embodiments, respective devices and/or servers of the system 100 may further include a display device (e.g., an LCD, an OLED, etc.), an input device (e.g., a touch device, a keyboard, a microphone, a mouse, etc.), a loudspeaker, or a vibration device and the like according to needs, which will not be limited here in the present disclosure.

Figure 2A:
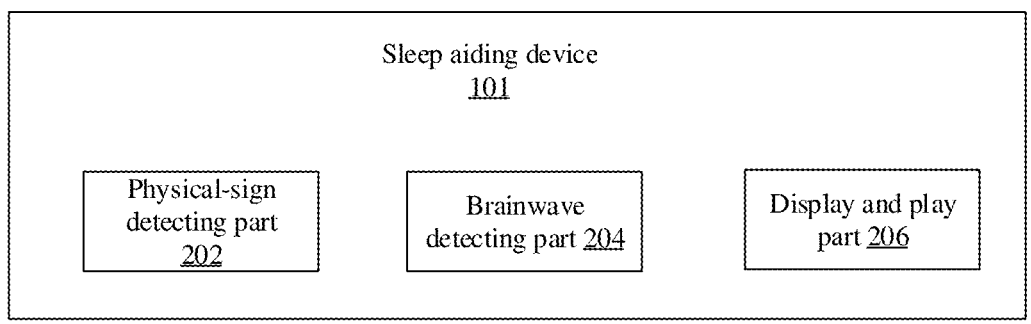
FIG. 2A to FIG. 2C are respectively schematic block diagrams of a sleep aiding device provided by various embodiments of the present disclosure.

As shown in FIG. 2A, the sleep aiding device 101 comprises: a physical-sign detecting part 202, configured to detect the user's physical sign data; a brainwave detecting part 204, configured to detect the user's brainwave signal data; and a display and play part 206, configured to receive a display and play instruction, and adjust at least one of a display mode and a play mode of the sleep aiding device according to the display and play instruction, wherein the display and play instruction is generated according to at least one of the physical sign data and the brainwave signal data.

For example, the user's physical sign data includes pulse signal data, body temperature data, blood pressure data, and/or any combination of the above data of the user. Of course, the user's physical sign data may also include other types of physical sign data, which will not be limited here in the present disclosure.

Figure 2B:
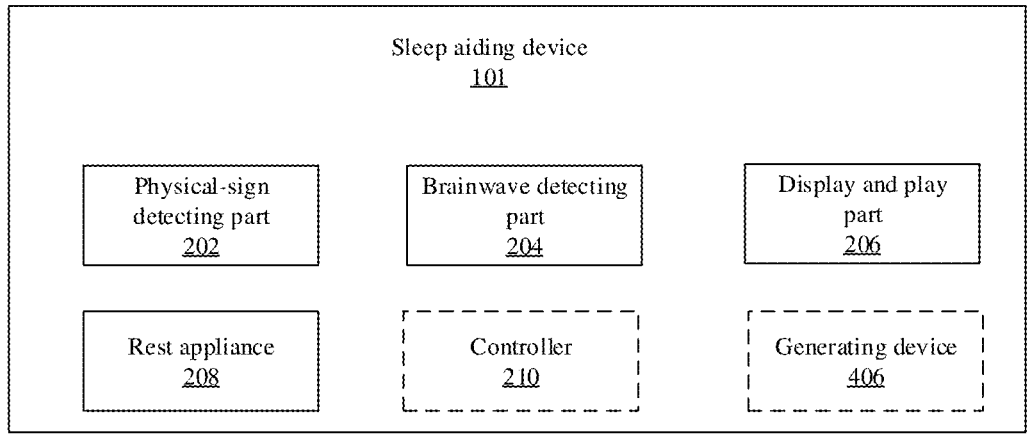

As shown in FIG. 2B, the sleep aiding device 101 may further comprise a rest appliance 208, and in some examples, may further comprise a controller 210 for controlling the rest appliance. The rest appliance 208 may include rotatable wheels mounted on its bottom, to facilitate movement of the rest appliance 208. The controller 210 may be a button or a remote controller for controlling movement of the rest appliance. For example, the rest appliance 208 may be a sofa or a bed which is movable or rotatable, with universal wheels mounted on the bottom, and with a control button mounted on an armrest side or a bed edge. Alternatively, the user may also control movement or rotation of the rest appliance 208 through the remote controller.

In some examples, the rest appliance 208 may further include a driving motor (not shown), for driving the rest appliance 208 to move or rotate. For example, the driving motor may be configured to control the rest appliance 208 to sway like a cradle according to the display and play instruction, such that a rhythm and a frequency of the swaying match the user's physical sign data and brainwave signal data. In other words, the rhythm and the frequency of the swaying of the rest appliance 208 match a sleep-awake degree of the user. For example, as the user gradually enters into the deep sleep state from the awake state, the frequency of the swaying of the rest appliance 208 gradually decreases and the swaying amplitude gradually decreases until the swaying is completely stopped.

Figure 4:
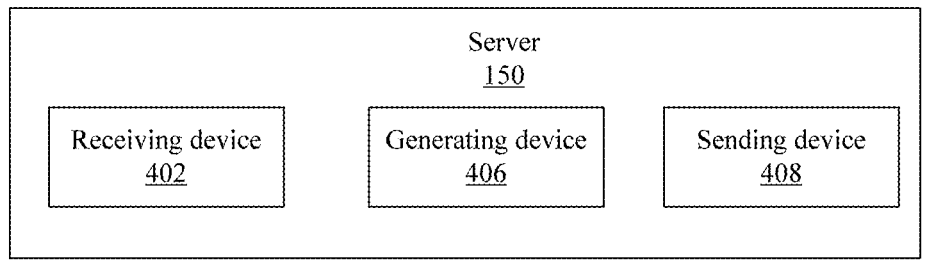
FIG. 4 is a schematic block diagram of a server provided by an embodiment of the present disclosure.
Figure 5:
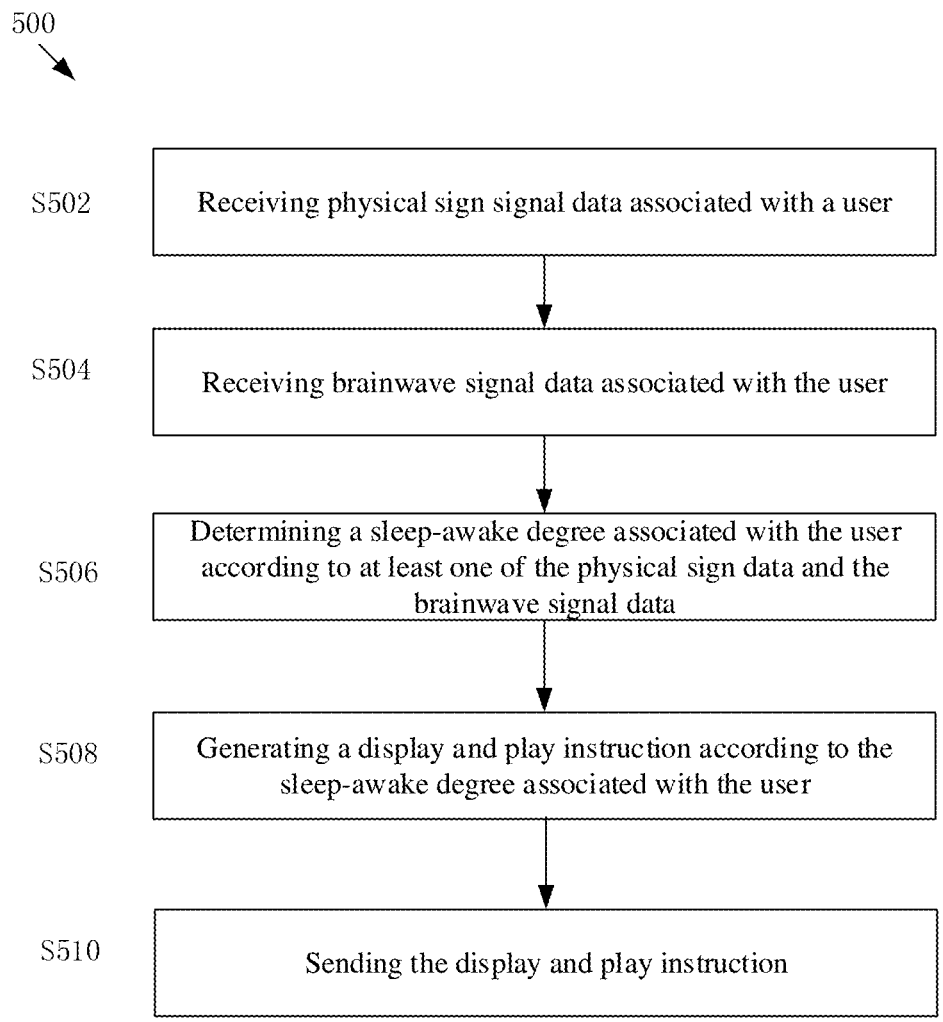
FIG. 5 is a flow chart of a server-side sleep aiding method provided by an embodiment of the present disclosure.

In some examples, the sleep aiding device 101 may further include a generating device 406 shown in a dotted line. The generating device 406 is configured to determine the sleep-awake degree of the user according to the physical sign data and the brainwave signal data, and generate the display and play instruction according to the sleep-awake degree of the user. That is to say, the display and play instruction may be generated locally at the sleep aiding device 101. In other examples, the generating device 406 may be located in the server 150, the display and play instruction is generated by the generating device 406 of the server 150, and the sleep aiding device 101 receives the display and play instruction from the server 150 (as shown in FIG. 4 to FIG. 5). Of course, one portion of the generating device 406 may be provided in the sleep aiding device 101, and another portion of the generating device 406 may be provided in the server 150. A function of the generating device 406 will be described in detail below in conjunction with FIG. 4.

Figure 2C:
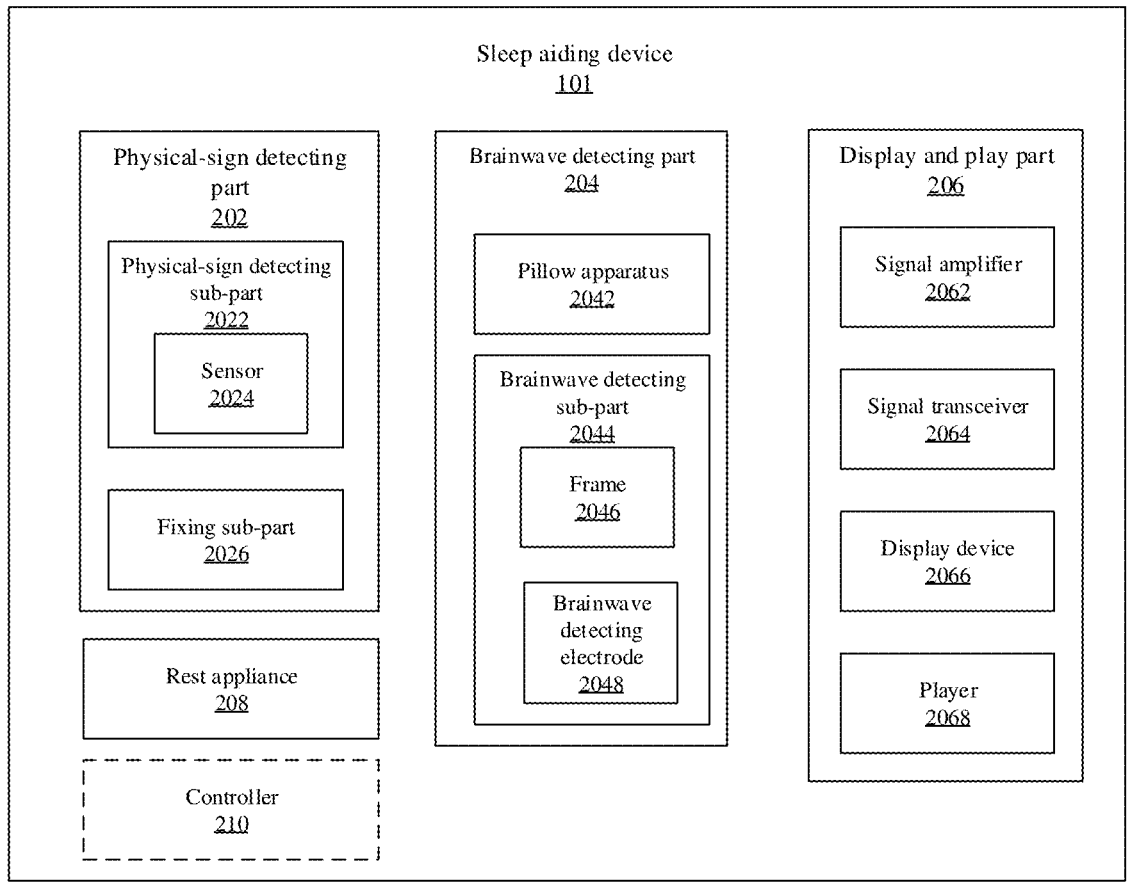

With reference to FIG. 2C, in the sleep aiding device 101, the physical-sign detecting part 202 includes a physical-sign detecting sub-part 2022. The physical-sign detecting sub-part 2022 includes an armlet, a bracelet, a wristband, a finger ring, a waistband, an anklet or other sub-parts, and the like, which will not be limited here in the present disclosure. The physical-sign detecting sub-part 2022 includes a sensor 2024 for detecting the user's physical sign data. The sensor 2024 may include a thermometer, a blood pressure meter, a pulse sensor, and the like.

In some examples, the physical-sign detecting sub-part 2022 is a stand-alone part that can be moved freely and communicate with other parts of the sleep aiding device 101 through a wireless network (e.g., WIFI, Bluetooth, etc.). In other examples, the physical-sign detecting sub-part 2022 is fixed into the sleep aiding device 101, and communicates with other parts of the sleep aiding device 101 through a wireless network or by wired transmission. For example, the physical-sign detecting part 202 further includes a fixing sub-part 2026, configured to fix the physical-sign detecting sub-part 2022 to the physical-sign detecting part 202, and fix the physical-sign detecting part 202 to the rest appliance 208.

For example, the physical-sign detecting part 202 is an arm-bearing physical-sign detecting part mounted on an outer edge of the rest appliance 208 (for example, the sofa or the bed), including the fixing sub-part (for example, a screw for fixing the armlet) and the physical-sign detecting sub-part (for example, the armlet). The fixing sub-part fixes the armlet, and fixes the arm-bearing physical-sign detecting part to the edge of the sofa or the bed. When the user is lying down, his/her arm may be stretched through the armlet, and sensors on the inner side of the armlet sense a pulse signal, body temperature data and other physical sign data of the user.

With continued reference to FIG. 2C, in the sleep aiding device 101, the brainwave detecting part 204 includes a pillow apparatus 2042 and a brainwave detecting sub-part 2044 connected with the pillow apparatus 2042. The brainwave detecting sub-part 2044 includes a frame 2046 and a brainwave detecting electrode 2048 fixed to the frame 2046. The brainwave detecting electrode 2048 is configured to detect the user's brainwave signal data.

The brainwave detecting sub-part 2044 sends the user's brainwave signal data to the server 150; or, the brainwave detecting sub-part 2044 sends the user's brainwave signal data to the display and play part 206, and the display and play part 206 (for example, a signal transceiver 2064 in the display and play part 206) sends the user's brainwave signal data to the server 150. Alternatively, the brainwave detecting sub-part 2044 sends the user's brainwave signal data to the generating device 406 located in the sleep aiding device 101 shown in FIG. 2B.

For example, the pillow apparatus 2042 is a headrest; the brainwave detecting sub-part 2044 is a brainwave detecting sub-part connected with the headrest, and includes the frame 2046 (for example, a head frame) and a brainwave detecting electrode 2048 fixed onto the head frame. When the user is lying down, his/her head is laid on the headrest and the head frame is worn, so that the brainwave detecting electrode in the head frame is in contact with the user's scalp to acquire his/her brainwave signal data. The brainwave detecting sub-part 2044 sends the brainwave signal data to the signal transceiver 2064 or directly sends the brainwave signal data to the server 150.

With continued reference to FIG. 2C, the display and play part 206 may be a self-adaptive display and play part, which is mounted on the physical-sign detecting part 202. Alternatively, the display and play part 206 is a detachable part, and is not fixed to the physical-sign detecting part 202. The display and play part 206 includes a signal amplifier 2062, the signal transceiver 2064, a display device 2066, and a player 2068.

The signal amplifier 2062 is configured to perform amplification processing on the physical sign data. The signal transceiver 2064 is configured to send the physical sign data after the amplification processing to the server 150, and receive the display and play instruction from the server 150. For example, the signal transceiver 2064 receives the physical sign data from the physical-sign detecting part 202, and at a same time, also receives the brainwave signal data from the brainwave detecting sub-part 2044, and sends the physical sign data and the brainwave signal data together to the server 150 or to the generating device 406 located in the sleep aiding device 101.

The display device 2066 is configured to activate and adjust the display mode according to the display and play instruction, so that the display mode matches the physical sign data and the brainwave signal data of the user. For example, the display device 2066 is configured to: in response to receiving the display and play instruction, activate the display mode of the sleep aiding device 101, and automatically rotate and detect a surrounding environment when activating the display mode; and adjust brightness of a display image according to brightness of the surrounding environment and/or the display and play instruction. For example, when the brightness of the surrounding environment is particularly low, the display device 2066 may increase or decrease the brightness of the display image. For another example, as the user gradually enters into the deep sleep state from the awake state, the display and play instruction may instruct the display device 2066 to gradually decrease the brightness of the display image until the display mode is deactivated.

For example, the display device 2066 includes a projecting device (e.g., a projector), a display (e.g., a television, an electronic screen, etc.) or other devices that may be used for displaying. The display mode includes: a projection mode in which the projecting device is used for projecting and/or a mode in which another display is used for displaying.

For example, the display device 2066 is further configured to: automatically rotate and detect the surrounding environment when activating the display mode, and display image content on a flat surface when detecting the flat surface. That is to say, when detecting the flat surface, the display device 2066 uses the flat surface as a projection plane. For example, the display device 2066 further includes a camera and an image processing device, the camera may automatically rotate to take a photograph of the surrounding environment, and the image processing device may recognize a structure having a flat surface, such as a wall, by processing and analyzing the photograph taken by the camera. For example, the image processing device may also acquire current brightness information of the surrounding environment by analyzing the photograph taken by the camera, and send the brightness information to the signal transceiver 2064. For another example, the sleep aiding device 101 may further include a sensor used for sensing the current brightness information of the surrounding environment and sending the brightness information to the signal transceiver 2064. The signal transceiver 2064 may send the brightness information to the server 150, or transmit the brightness information to the generating device 406 in the sleep aiding device 101.

The player 2068 is configured to activate and adjust a play mode according to the display and play instruction, so that the play mode matches the physical sign data and the brainwave signal data of the user. For example, the player 2068 is configured to: when activating the play mode, adjust the play content and the play volume according to the display and play instruction. For example, as the user gradually enters into the deep sleep state from the awake state, the display and play instruction may instruct the player 2068 to gradually lower the volume and switch the play content, until the play mode is deactivated.

For example, image content displayed by the display device 2066 includes one or more of pre-stored content, content obtained through the network, and content played by the television. Content played by the player 2068 includes one or more of pre-stored content, content obtained through the network, and content played by the television. The display content and the play content will not be limited here in the present disclosure.

For example, the display and play instruction may instruct one or more of the turning-on or turning-off of a display function, the content of the displayed image and its source, the brightness of the displayed image, the turning-on or turning-off of a play function, the play content and its source, or the play volume. The display and play instruction may further include other instructions, which will not be limited here in the present disclosure.

It is worth noting that, although not shown in FIG. 2A to FIG. 2C, respective parts or sub-parts in the sleep aiding device 101 may be connected with one another and may communicate with and transmit data and signals to one another.

Figure 3:
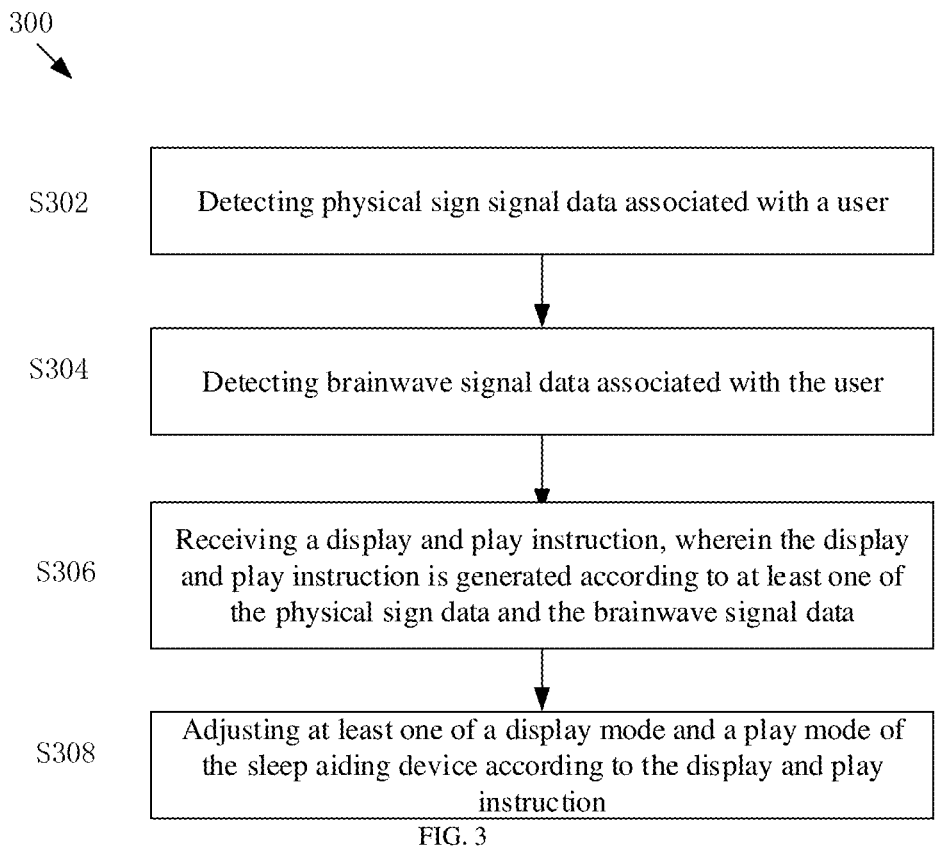
FIG. 3 is a flow chart of a sleep aiding method provided by an embodiment of the present disclosure.

As shown in FIG. 3, an embodiment of the present disclosure further provides a sleep aiding method 300, used in any one of the above-described sleep aiding devices. The method comprises: S302, detecting a user's physical sign data; S304, detecting the user's brainwave signal data; S306, receiving a display and play instruction, wherein the display and play instruction is generated according to at least one of the physical sign data and the brainwave signal data; and S308, adjusting at least one of a display mode and a play mode of the sleep aiding device according to the display and play instruction.

For example, before receiving the display and play instruction, the method further comprises: performing amplification processing on the detected physical sign data; sending the physical sign data after the amplification processing to a server; and sending the user's brainwave signal data to the server.

For example, the method comprises: receiving the display and play instruction from the server. Alternatively, the method further comprises: determining a sleep-awake degree of the user according to the detected physical sign data and brainwave signal data; and automatically generating the display and play instruction locally according to the sleep-awake degree of the user.

For example, the method further comprises: activating the display mode of the sleep aiding device 101 in response to receiving the display and play instruction, and automatically rotating and detecting a surrounding environment when activating the display mode; and adjusting brightness of a display image according to brightness of the surrounding environment and/or the user's sleep-awake degree.

For example, the method further comprises: activating the play mode of the sleep aiding device 101 in response to receiving the display and play instruction; and adjusting the play mode according to the display and play instruction, so that the play mode matches the physical sign data and the brainwave signal data of the user. For example, by using the method, the play content and the play volume may be adjusted according to the sleep-awake degree of the user. For example, as the user gradually enters into the deep sleep state from the awake state, by using the method, the volume may be gradually lowered and the play content may be switched, until the play mode is deactivated.

As shown in FIG. 4, an embodiment of the present disclosure further provides a server 150, comprising: a receiving device 402, configured to receive physical sign data and brainwave signal data of a user; a generating device 406, configured to determine a sleep-awake degree of the user according to the physical sign data and the brainwave signal data, and generate a display and play instruction according to the sleep-awake degree of the user; and a sending device 408, configured to send the display and play instruction.

In some examples, the generating device 406 acquires the physical sign data and the brainwave signal data of the user, and compares and maps the data with a preset data table of respective stages of an awake state and a sleep state of a human body, so as to determine a current sleep-awake degree of the user (e.g., fully awake, shallow sleep, or deep sleep, etc.). For example, when the user's pulse data coincides with pre-stored pulse data when the human body enters deep sleep, and the user's brainwave signal data coincides with pre-stored brainwave signal data when the human body enters deep sleep, the generating device 406 determines that the user is in the deep sleep state.

It is worth noting that, the preset data table of respective stages of the awake state and the sleep state of the human body may be obtained in advance through experimental measurements and stored in a memory. For example, by monitoring sleep of a large number of volunteers, physical sign data and brainwave signal data of respective volunteers when they are in different sleep-awake degrees (e.g., fully awake, shallow sleep, or deep sleep) are collected, and the collected data is organized into a tabular form. By taking the pulse data and the brainwave signal data as an example, an exemplary table is shown below:

| Sleep-awake degree | Range of pulse data | Brainwave signal data |
| --- | --- | --- |
| Fully awake | 60 to 100 beats/minute | Brainwaves are α waves |
| Shallow sleep | 60 to 100 beats/minute | Brainwaves are mainly α waves, with a small amount of δ waves |
| Deep sleep | 55 to 65 beats/minute | Brainwaves are δ waves |

Of course, it is also possible to collect the physical sign data and the brainwave signal data related to the user of the sleep aiding device in advance when the user is in different sleep-awake degrees, and then organize the collected data into a tabular form.

The generating device 406 generates the display and play instruction according to the current sleep-awake degree of the user. The display and play instruction may instruct the display content (e.g., projected content), image brightness, the play volume, play sound/music genre, and turning on or off of the display and/or play function. The sending device 408 sends the display and play instruction to the sleep aiding device 101. Therefore, through the indication of the display and play instruction, both the display mode and the play mode of the sleep aiding device 101 may be matched with the current sleep-awake degree of the user.

In some examples, the sleep aiding device 101 may send current brightness information of a surrounding environment in which the user is located to the server 150. The generating device 406 may determine an amount of brightness of the display image to be adjusted according to the current sleep-awake degree of the user and the current brightness information of the user's surrounding environment, and then generate the display and play instruction accordingly.

For example, the receiving device 402 and the sending device 408 may be integrated as a transceiving device, which may include, for example, a wireless transceiver or a network adapter, and the like.

In some embodiments of the present disclosure, the receiving device 402, the generating device 406, and the sending device 408 may include codes and programs stored in a memory; the processor may execute the codes and the programs to implement some or all of the functions of the receiving device 402, the generating device 406 and the sending device 408 as described above.

For example, the receiving device 402, the generating device 406 and the sending device 408 may also be dedicated hardware devices for implementing some or all of the functions of the receiving device 402, the generating device 406 and the sending device 408 as described above. For example, the receiving device 402, the generating device 406 and the sending device 408 may be a single circuit board or a combination of a plurality of circuit boards for implementing the above-described functions. In the embodiments of the present disclosure, the single circuit board or the combination of a plurality of circuit boards may include: (1) one or more processors; (2) one or more non-transitory computer readable memories connected with the processor; and (3) processor-executable firmware stored in the memory.

As shown in FIG. 5, an embodiment of the present disclosure further provides a server-side sleep aiding service method 500, used in the above-described server. The method 500 comprises: S502, receiving physical sign data associated with a user; S504, receiving brainwave signal data associated with the user; S506, determining a sleep-awake degree associated with the user according to the physical sign data and the brainwave signal data; S508, generating a display and play instruction according to the sleep-awake degree associated with the user; and S510, sending the display and play instruction.

Figure 6:
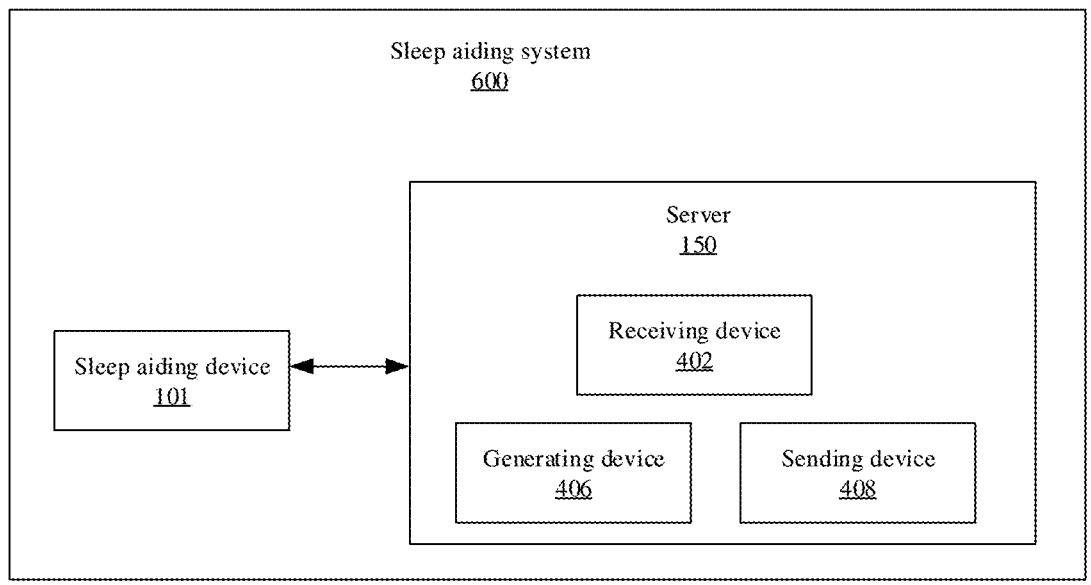
FIG. 6 is a schematic block diagram of a sleep aiding system provided by an embodiment of the present disclosure.

As shown in FIG. 6, an embodiment of the present disclosure further provides a sleep aiding service system 600, comprising: any sleep aiding device 101 as described above; and a server 150. The server 150 includes the receiving device 402, configured to receive physical sign data and brainwave signal data of a user; the generating device 406, configured to determine a sleep-awake degree of the user according to the physical sign data and the brainwave signal data, and generate a display and play instruction according to the sleep-awake degree of the user; and the sending device 408, configured to send the display and play instruction. For example, the sleep aiding device 101 and the server 150 may communicate through a network 160; or, the sleep aiding device 101 and the server 150 may directly communicate with each other.

Figure 7:
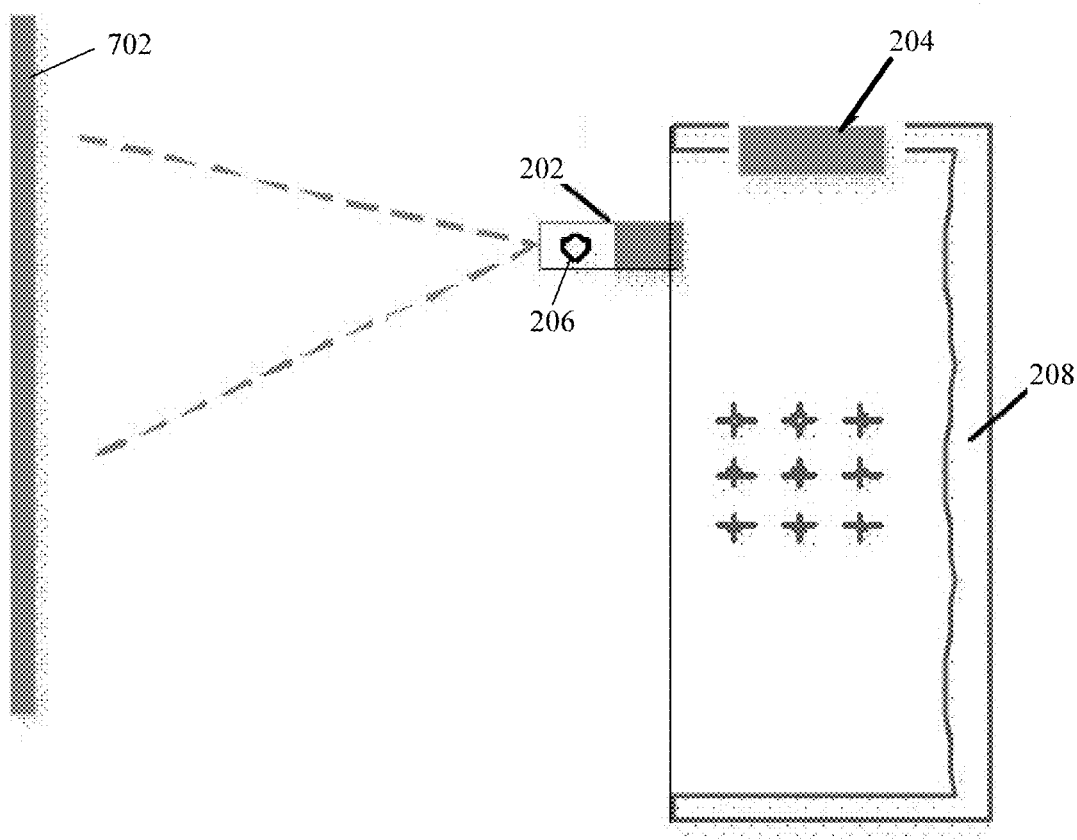
FIG. 7 is a schematic diagram of a sleep aiding device provided by an embodiment of the present disclosure.

FIG. 7 is a schematic diagram of the sleep aiding device 101 provided by an embodiment of the present disclosure. The physical-sign detecting part 202 is an arm-bearing physical-sign detecting part mounted on an outer edge of a rest appliance 208 (for example, a sofa or a bed). The brainwave detecting part 204 is provided in a pillow shape. The display and play part 206 is provided in the physical-sign detecting part 202. The display and play part 206 is configured to project onto a projection plane 702.

Figure 8:
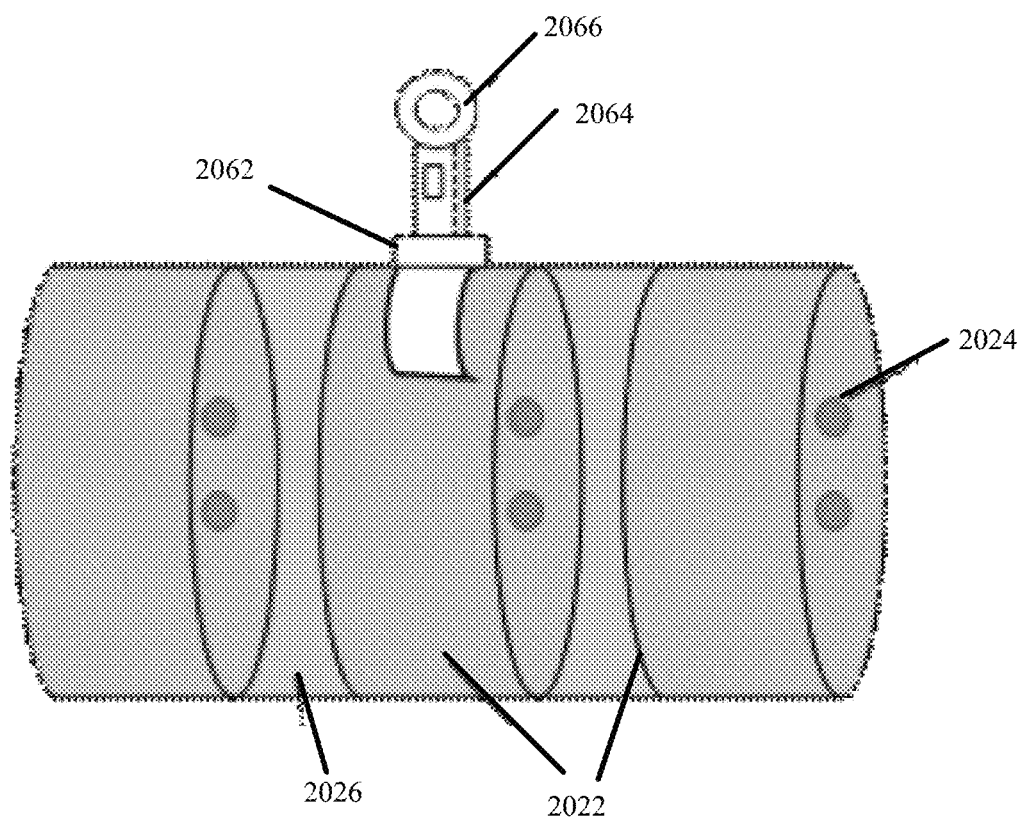
FIG. 8 is a schematic diagram of a physical-sign detecting part and a display and play part provided by an embodiment of the present disclosure.

With reference to FIG. 8, the physical-sign detecting part 202 includes a fixing sub-part 2026 and a physical-sign detecting sub-part 2022 (e.g., an armlet). The fixing sub-part 2026 fixes the armlet itself, and fixes the arm-bearing physical-sign detecting part to the edge of the sofa or the bed. A sensor 2024 is provided on the inner side of the physical-sign detecting sub-part 2022. A signal amplifier 2062, a signal transceiver 2064 and a display device 2066 of the display and play part 206 are all fixed to the physical-sign detecting part 202.

Figure 9:
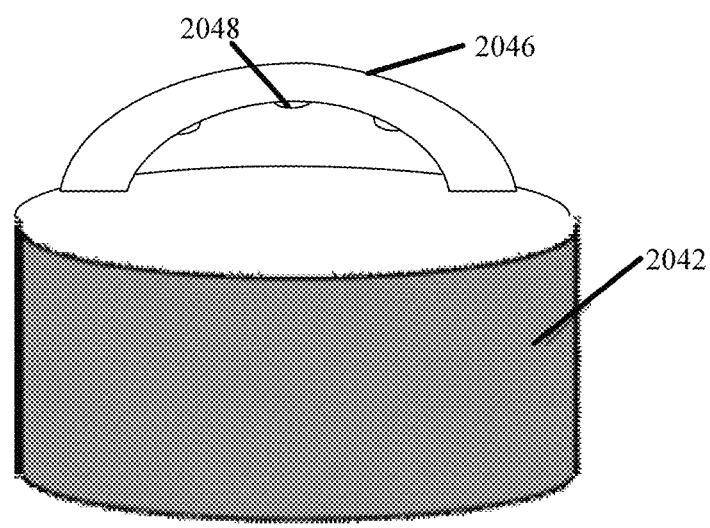
FIG. 9 is a schematic diagram of a brainwave detecting part provided by an embodiment of the present disclosure.

With reference to FIG. 9, the pillow apparatus 2042 of the brainwave detecting part 204 is a headrest; the brainwave detecting sub-part 2044 includes a frame 2046 (for example, a head frame) and a brainwave detecting electrode 2048 fixed onto the head frame. When the user is lying down, his/her head is laid on the headrest and the head frame is worn, so that the brainwave detecting electrode in the head frame is in contact with the user's scalp to acquire his/her brainwave signal data.

In summary, the sleep aiding device and the method thereof, the server and the method thereof, and the sleep aiding system provided by the embodiments of the present disclosure, are capable of automatically adjusting the display mode and the play mode according to changes in the sleep-awake degree of the user, so that both the display mode and the play mode match the user's current sleep-awake degree, to help the user fall asleep quickly, and improve the sleep quality.

In the present disclosure, terms such as "first", "second" and the like used in the present disclosure do not indicate any sequence, quantity or significance but only for distinguishing different constituent parts. Also, the terms such as "a," "an," or "the" etc., are not intended to limit the amount, but indicate the existence of at least one. The terms "comprises," "comprising," "includes," "including," etc., are intended to specify that the elements or the objects stated before these terms and encompass the elements or the objects and equivalents thereof listed after these terms, but do not preclude the other elements or objects.

It is noted that, azimuth or positional relationships indicated by terms such as "up" and "down" and so on, are azimuth or positional relationships based on the drawings, which are only to facilitate description of the embodiments of the present disclosure and simplify the description, but not to indicate or imply that the devices or components must have a specific azimuth, or be constructed or operated in the specific azimuth, which thus cannot be understood as a limitation to the embodiments of the present disclosure. Unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. Those skilled in the art can understand the specific meanings of the above-mentioned terms in the embodiments of the present disclosure according to the specific circumstances.

Obviously, those skilled in the art may modify the disclosure in various ways without breaking away from the spirits and scope of the disclosure. And so, if these changes and variations of the disclosure also fall within the scope of the claims or their equivalent technologies, the disclosure intends to include these changes and variations.

What are described above is related to the illustrative embodiments of the disclosure only and not limitative to the scope of the disclosure; any changes or replacements easily for those technical personnel who are familiar with this technology in the field to envisage in the scopes of the disclosure, should be in the scope of protection of the present disclosure. Therefore, the scopes of the disclosure are defined by the accompanying claims.

The present application claims the priority of the Chinese Patent Application No. 201710325922.3 filed on May 10, 2017, which is incorporated herein by reference in its entirety as part of the disclosure of the present application.

The invention claimed is:

1. A sleep aiding device, comprising:
a physical-sign detecting part, configured to detect physical sign data associated with a user;
a brainwave detecting part, configured to detect brainwave signal data associated with the user; and
a display and play part, configured to:
receive a display and play instruction, wherein the display and play instruction is generated according to the physical sign data and the brainwave signal data; and
adjust at least one selected from the group consisting of a display mode and a play mode of the sleep aiding device according to the display and play instruction, wherein the display and play part includes a display device, a player, and a signal amplifier, and the signal amplifier is configured to perform amplification processing on the physical sign data;
the display device is further configured to:
automatically rotate and detect a surrounding environment when activating the display mode; and
adjust brightness of a display image according to at least one selected from the group consisting of brightness of the surrounding environment and the display and play instruction; and
the player is further configured to:
adjust play content and play volume according to the display and play instruction when activating the play mode.

2. The sleep aiding device according to claim 1, further comprising a rest appliance.

3. The sleep aiding device according to claim 2, wherein:
the physical-sign detecting part includes a physical-sign detecting sub-part; and
the physical-sign detecting sub-part includes a sensor configured for detecting the physical sign data associated with the user.

4. The sleep aiding device according to claim 2, wherein:
the brainwave detecting part includes a pillow apparatus and a brainwave detecting sub-part connected with the pillow apparatus;
the brainwave detecting sub-part includes a frame and a brainwave detecting electrode fixed to the frame; and
the brainwave detecting electrode is configured to detect the brainwave signal data associated with the user.

5. The sleep aiding device according to claim 2, wherein the display and play part further includes a signal transceiver;
the signal transceiver is configured to send the physical sign data after amplification processing to the server, and receive the display and play instruction from the server;
the display device is configured to activate and adjust the display mode according to the display and play instruction, so that the display mode matches the physical sign data and the brainwave signal data associated with the user; and
the player is configured to activate and adjust the play mode according to the display and play instruction, so that the play mode matches the physical sign data and the brainwave signal data associated with the user.

6. The sleep aiding device according to claim 1, wherein:
the physical-sign detecting part includes a physical-sign detecting sub-part; and
the physical-sign detecting sub-part includes a sensor configured for detecting the physical sign data associated with the user.

7. The sleep aiding device according to claim 6, wherein:
the physical-sign detecting part further includes a fixing sub-part; and
the fixing sub-part is configured to fix the physical-sign detecting sub-part to the physical-sign detecting part, and fix the physical-sign detecting part to the rest appliance.

8. The sleep aiding device according to claim 1, wherein:
the brainwave detecting part includes a pillow apparatus and a brainwave detecting sub-part connected with the pillow apparatus;
the brainwave detecting sub-part includes a frame and a brainwave detecting electrode fixed to the frame; and
the brainwave detecting electrode is configured to detect the brainwave signal data associated with the user.

9. The sleep aiding device according to claim 8, wherein:
the brainwave detecting sub-part sends the brainwave signal data associated with the user to a server; or
the brainwave detecting sub-part sends the brainwave signal data associated with the user to the display and play part, and the display and play part sends the brainwave signal data associated with the user to the server.

10. The sleep aiding device according to claim 1, wherein the display and play part further includes a signal transceiver;
the signal transceiver is configured to send the physical sign data after amplification processing to a server, and receive the display and play instruction from the server;
the display device is configured to activate and adjust the display mode according to the display and play instruction, so that the display mode matches the physical sign data and the brainwave signal data associated with the user; and
the player is configured to activate and adjust the play mode according to the display and play instruction, so that the play mode matches the physical sign data and the brainwave signal data associated with the user.

11. The sleep aiding device according to claim 10, wherein the display device includes a projecting device or a display.

12. The sleep aiding device according to claim 1, wherein content of the display image and the play content each include at least one selected from the group consisting of pre-stored content, content obtained through a network, and content played by a television.

13. The sleep aiding device according to claim 1, wherein the physical sign data associated with the user includes at least one selected from the group consisting of pulse signal data, body temperature data, or blood pressure data associated with the user.

14. The sleep aiding device according to claim 1, wherein the display and play instruction instructs at least one selected from the group consisting of turning on or off of a display function, the content and a source of a display image, brightness of the display image, turning on or off of a play function, play content and its source, or a play volume.

15. A sleep aiding method, used in the sleep aiding device according to claim 1, comprising:

detecting physical sign data associated with a user;
detecting brainwave signal data associated with the user;
receiving a display and play instruction, wherein the display and play instruction is generated according to the physical sign data and the brainwave signal data; and
adjusting at least one selected from the group consisting of a display mode and a play mode of the sleep aiding device according to the display and play instruction.

16. The sleep aiding method according to claim 15, wherein before receiving the display and play instruction, the method further comprises:
performing amplification processing on the detected physical sign data;
sending the physical sign data after amplification processing to a server; and
sending the brainwave signal data associated with the user to the server.

17. A sleep aiding service system, comprising: a sleep aiding device and a server, wherein
the sleep aiding device comprises:
a physical-sign detecting part, configured to detect physical sign data associated with a user;
a brainwave detecting part, configured to detect brainwave signal data associated with the user; and
a display and play part, configured to:
receive a display and play instruction, wherein the display and play instruction is generated according to the physical sign data and the brainwave signal data; and
adjust at least one selected from the group consisting of a display mode and a play mode of the sleep aiding device according to the display and play instruction, wherein the display and play part includes a display device, a player, and a signal amplifier, and the signal amplifier is configured to perform amplification processing on the physical sign data;
the display device is further configured to:
automatically rotate and detect a surrounding environment when activating the display mode; and
adjust brightness of a display image according to at least one selected from the group consisting of brightness of the surrounding environment and the display and play instruction; and
the player is further configured to:
adjust play content and play volume according to the display and play instruction when activating the play mode, and
the server comprises:
a receiving device, configured to receive physical sign data and brainwave signal data associated with a user;
a generating device, configured to determine a sleep-awake degree associated with the user according to the physical sign data and the brainwave signal data, and generate a display and play instruction according to the sleep-awake degree associated with the user; and
a sending device, configured to send the display and play instruction.

* * * * *